United States Patent [19]

Stanners et al.

[11] Patent Number: 5,330,440
[45] Date of Patent: Jul. 19, 1994

[54] REVERSE THREAD CARPULE DENTAL SAFETY SYRINGE

[76] Inventors: Sydney D. Stanners, Box 11, 9169 Barnes Place, Sidney, B. C., Canada, V8L 4X7; Arthur Makosinski; Rodney Katz, both c/o The University of Victoria, P.O. Box 3055, Victoria, B. C., Canada, V8W 3P6

[21] Appl. No.: 963,966

[22] Filed: Oct. 21, 1992

[51] Int. Cl.$^5$ .............................................. A61M 5/32
[52] U.S. Cl. ..................................... 604/195; 604/110; 604/192; 604/196
[58] Field of Search ................... 433/80, 87, 89, 90, 433/116; 604/110, 194–199, 192, 263, 226, 218, 221–222, 231–232

[56] References Cited

U.S. PATENT DOCUMENTS 5,125,908  6/1992  Cohen ................................. 609/196
5,167,641 12/1992  Schmitz .............................. 604/196
5,263,933 11/1993  Novacek et al. ................... 604/110

FOREIGN PATENT DOCUMENTS 0617857  6/1980  Switzerland ......................... 433/89
2210268  6/1989  United Kingdom ................ 604/197

Primary Examiner—C. Fred Rosenbaum
Assistant Examiner—Vanitha Alexander
Attorney, Agent, or Firm—Oyen Wiggs Green & Mutala

[57] ABSTRACT

This invention pertains to a novel reverse thread carpule dental safety syringe which is useful to dentists in freezing the gums of their patients prior to performing dental work on the patients' teeth, and subsequently retracting the needle into the carpule. A dental syringe for use with a carpule comprising: (a) a hollow barrel; (b) a handle and plunger adapted to reciprocate within the barrel, the end of the plunger removed from the handle being adapted to releasably engage with a first end of a carpule; (c) a carpule receiving cavity at one end of the barrel in alignment with the plunger; and (d) an engagement member at the end of the barrel opposite the handle and plunger for releasably engaging a second end of a carpule.

16 Claims, 7 Drawing Sheets

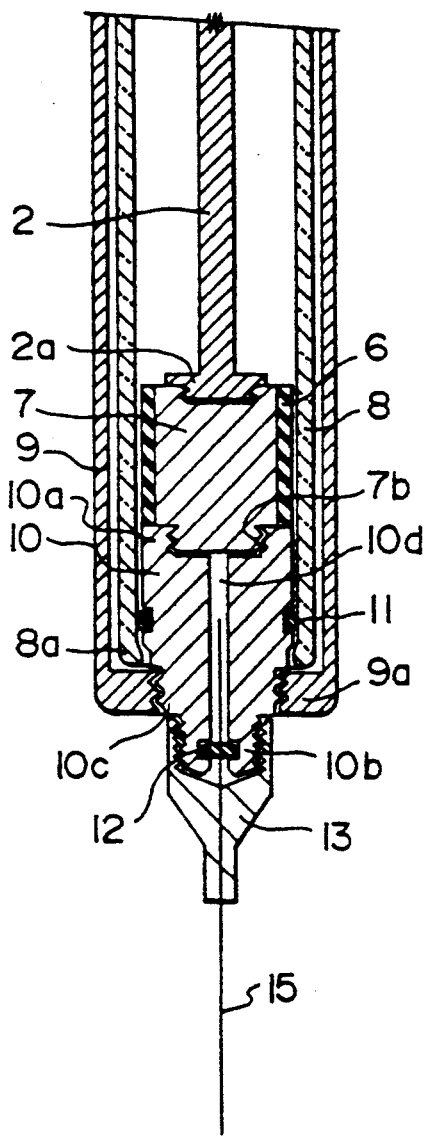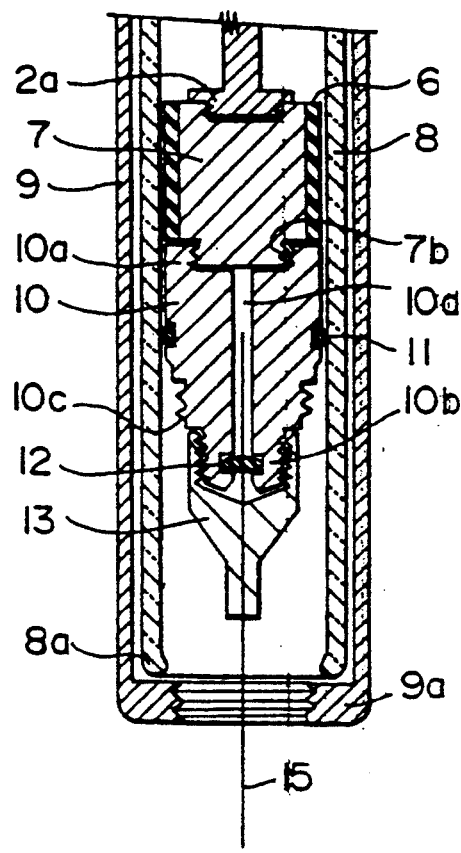
FIG.6
FIG.7

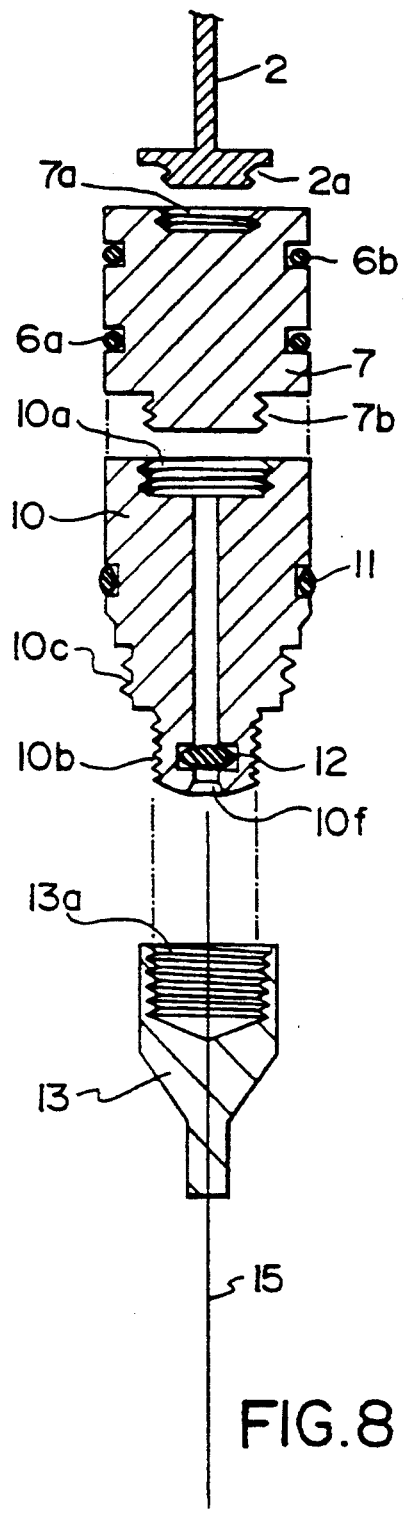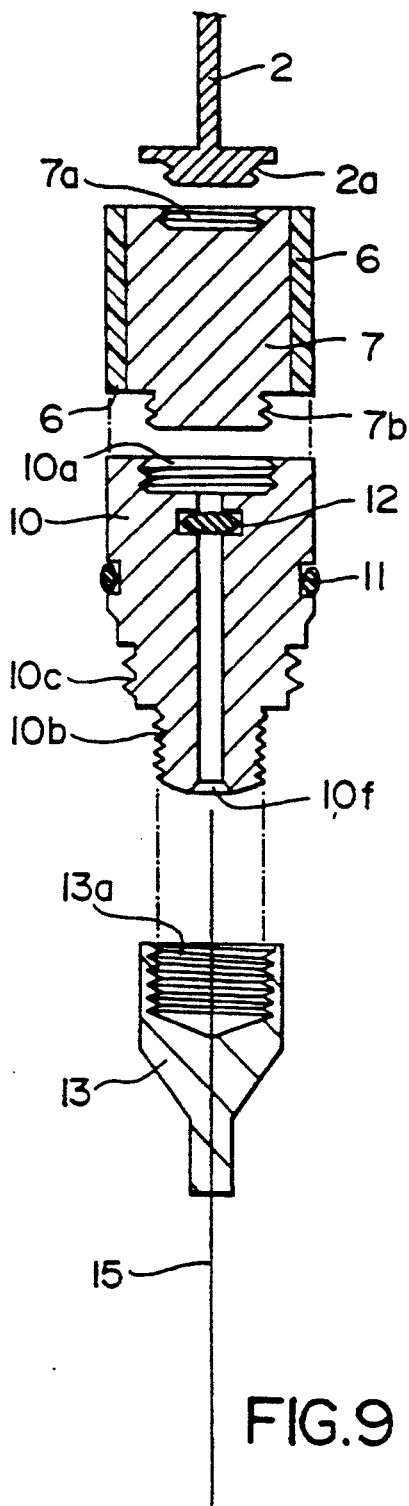

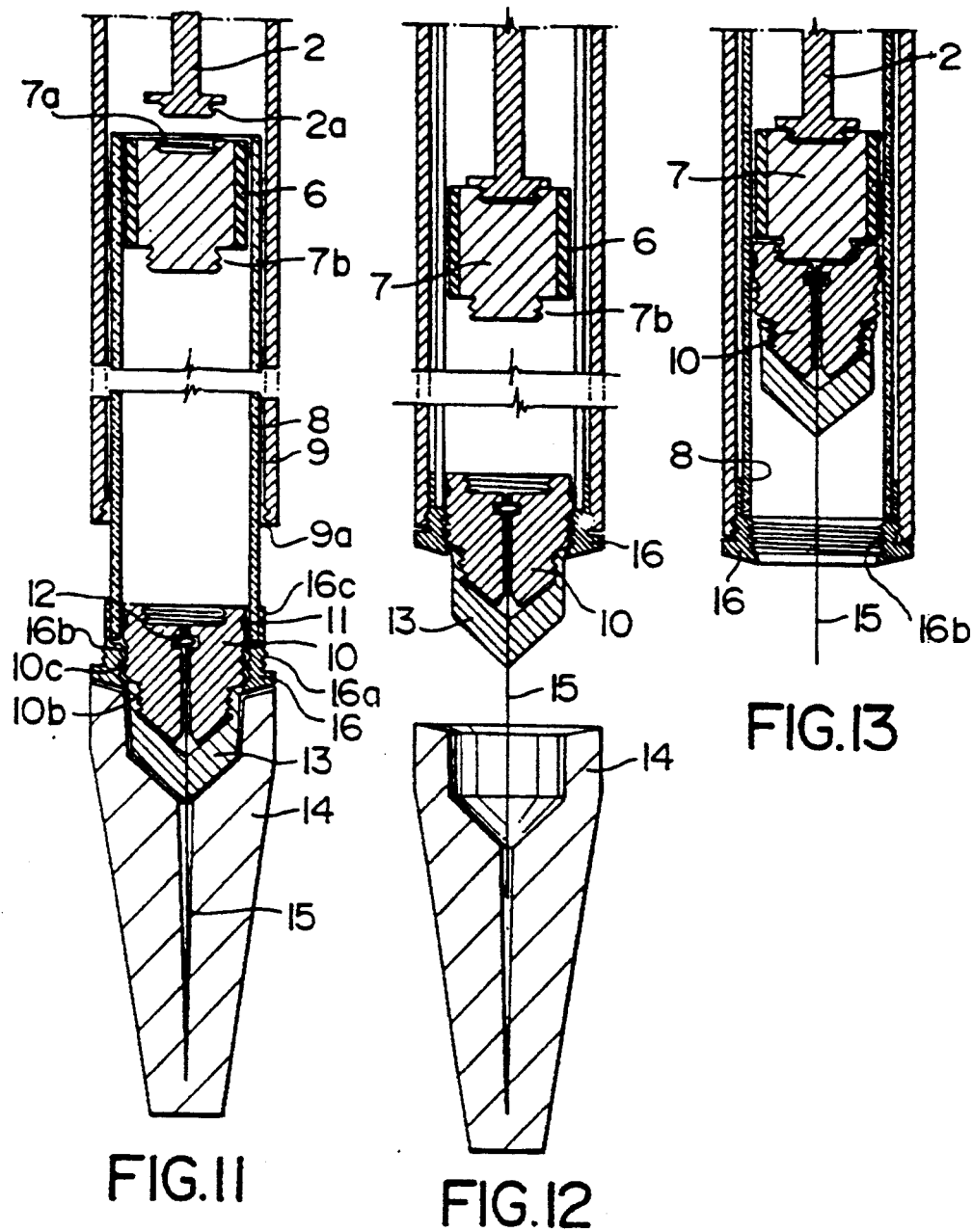

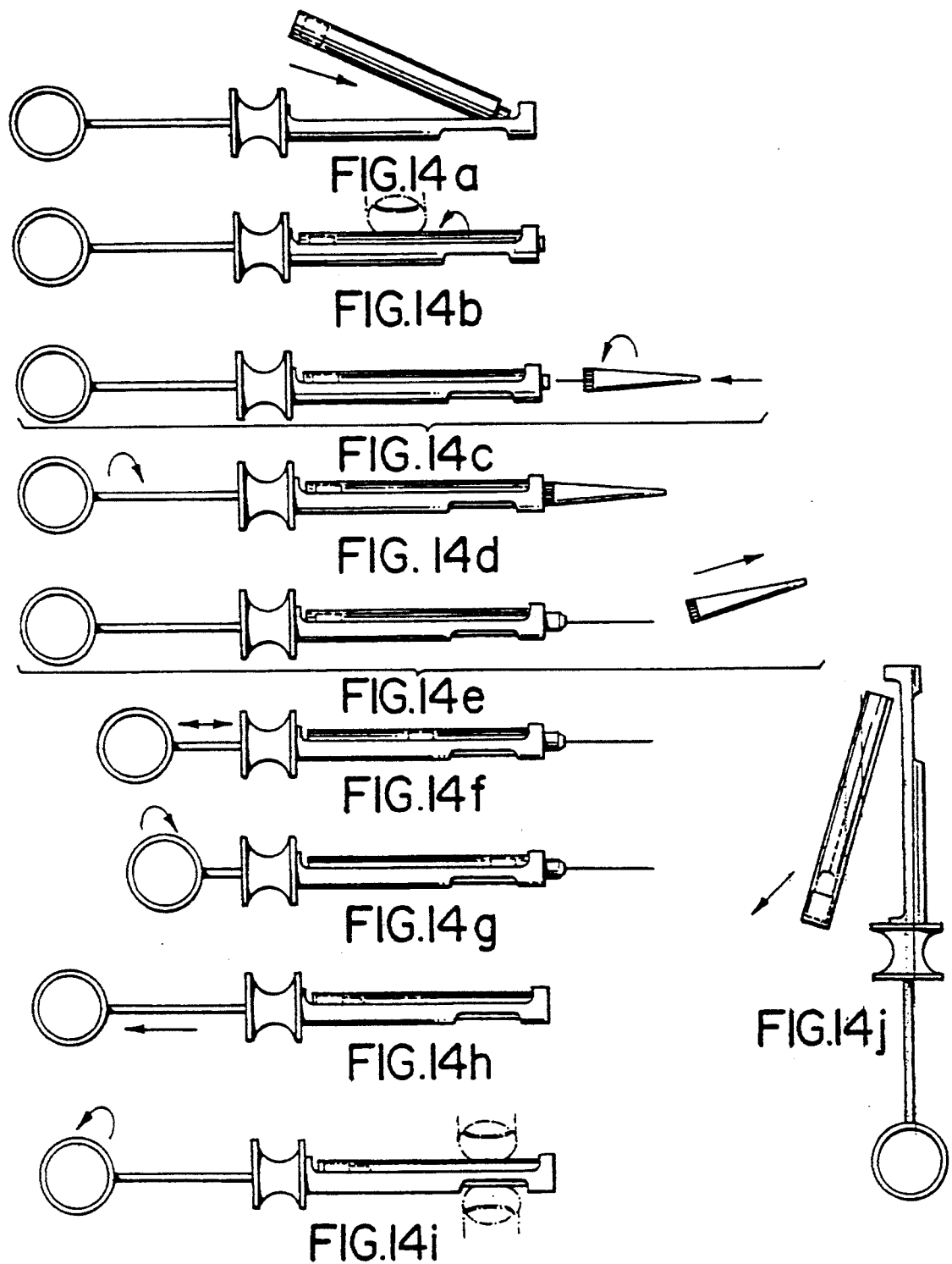

REVERSE THREAD CARPULE DENTAL SAFETY SYRINGE

FIELD OF THE INVENTION

This invention pertains to a novel reverse thread carpule dental safety syringe which is useful to dentists in freezing the gums of their patients prior to performing dental work on the patients' teeth, and subsequently retracting the needle into the carpule.

BACKGROUND OF THE INVENTION

Needle stick injury is one of the most common occupational health hazards among health care professionals. Those involved in both the dental and medical professions are constantly at risk of dangerous patient-to-staff transmission of AIDS, hepatitis-B and other blood borne diseases from a contaminated needle.

In recent years, with the increase in dangerous communicable diseases, and particularly the growth of the fatal disease known as AIDS (acquired immune deficiency syndrome), it has become critical to eliminate the incidence of needlestick injuries to personnel. In the medical profession, and elsewhere, due to contaminated needles of used syringes. There is a constant risk to the medical profession of contracting the disease of an infected patient by being scratched or pricked from the contaminated needle of a used syringe.

A number of designs of syringes which include features for protecting the exposed needle after use of the syringe have been developed and patented in recent years. The following patents are exemplary and not exhaustive.

U.S. Pat. No. 4,655,751, granted Apr. 7, 1987, Harbaugh, discloses a syringe which has a concentric protective shell over the barrel of the syringe. The shell is spaced outwardly from the barrel of the syringe and is slidable between a first needle-exposing position and a second needle-covering position. The shell has windows or a grid to permit viewing of the barrel of the syringe. A number of spacer ears on the barrel's outer surface permit the shell to be temporarily locked into mating pockets with the barrel.

U.S. Pat. No. 4,631,057, granted Dec. 23, 1986, Sampson, discloses an apparatus for injecting a substance into a human or animal. The apparatus includes a body, a needle coupled to the body, and a needle guard mounted on the body for movement from a retracted position in which the guard does not shield the needle to an extended position in which the guard shields the needle. The needle guard can be releasable retained in the retracted position and locked in the extended position. Locking of the needle guard is accomplished by interlocking members carried by the needle guard and by a collar mounted on the body.

U.S. Pat. No. 4,573,976, granted Mar. 4, 1986, Sampson, protects a syringe design which has a needle guard mounted on the body of the syringe, the guard being extendible so that it obstructs access to the point of the needle. The guard can be retracted over the barrel of the syringe to expose the point of the needle. Interlocking members on the body and the guard permit the guard to be releasably locked in the retracted or the extended position.

U.S. Pat. No. 4,425,120, granted Jan. 10, 1984, Sampson, discloses a hypodermic syringe comprising a barrel, a needle coupled to the barrel, and a needle guard mounted on the barrel for movement between an extended position in which the guard shields the needle, and a retracted position in which the guard does not shield the needle. The guard can be locked in either the extended or the retracted position. Locking of the guard is accomplished by a track on the internal surface of the guard and a track engaging member on the barrel.

U.S. Pat. No. 4,859,182, Nerli, discloses a dental syringe of the type having a beak for dispensing fluids into an oral cavity. The syringe comprises a sheath, the sheath being a form fitted, generally elongated tube or cylinder adapted to substantially fit over and cover the beak. The sheath is removably attached to the beak, and provides a substantially sterile outer-covering for the beak. The sheath has an open end and a terminal end having an aperture to allow a fluid to be dispensed from the beak and the sheath. The aperture is located near a discharge orifice of the beak through which the fluid is dispensed. The tip is located at the terminal end of the sheath, the tip and the sheath providing a substantially sterile outer-covering for the beak and the discharge orifice. The tip has a valve coincident with the discharge orifice. The valve allows the fluid to be dispensed from the beak and the tip. The valve substantially prevents contaminants from entering or being drawn into the beak through the discharge orifice.

U.S. Pat. No. 4,826,490, Byrne etal., discloses a safety device for a hypodermic needle. Byrne discloses a disposable non-reusable hypodermic needle assembly comprising: a needle support housing having a connector formation for removable attachment with the apparatus; a hypodermic needle supported by the housing for communication with the apparatus by way of the formation, one end portion of the needle projects from the housing remotely from the formation, and a sheath surrounding the housing and mounted thereon for movement in the longitudinal direction of the needle from a first position nearer to the formation and in which first position the needle one end portion is exposed, to a second position further from the formation and in which second position the needle end is enclosed within the sheath.

U.S. Pat. No. 4,907,968, Elsnet, discloses a dental syringe shield or prophylactic which has a removable disposable dental syringe shield for placement over and in proximate contact with the nozzle of a dental syringe. The design includes an elongated cylindrical portion for fitting over the nozzle of the dental syringe and a barrel portion for fitting over the nozzle securing means of the dental syringe. The design also includes a backsplash collar shield, which fits over the nozzle portion and abuts the front of the base portion of the dental syringe.

U.S. Pat. No. 4,898,590, Andors, discloses a syringe comprising: a barrel including longitudinal walls defining an elongate chamber therein for receiving a cartridge; a first, elongate opening defined within the longitudinal walls through which a cartridge may be insetted into the chamber; a second opening defined within the longitudinal walls of the barrel, the second opening in opposing relation to the first elongate opening; and a sleeve slidably mounted to the barrel. The sleeve includes a first elongate opening and a second opening; the second sleeve opening being in opposing relation to the first elongate sleeve opening, the sleeve is movable to a position with respect to the barrel such that the first and second sleeve openings are substantially in register with the first and second barrel openings. The design includes means for retaining the sleeve upon the barrel.

U.S. Pat. No. 4,915,702, Haber etal. discloses a shielded safety syringe comprising an inner syringe cylinder having proximal and distal ends, a hypodermic needle supported at and extending outwardly from the distal end, and an outer protective sleeve having proximal and distal ends. The outer sleeve coaxially aligns with an axially advanceable relative to the inner cylinder from a retracted position, where the needle projects outwardly through an opening in the distal end of the sleeve, to an extended position, where the needle is located within and completely surrounded by the sleeve. A first groove is formed in the inner cylinder and locking means are pivotally interconnected with the outer sleeve and rotatable between unlocked and locked conditions, the locking means rotated to the locked condition for receipt within the groove formed in the inner cylinder when the outer sleeve is advanced axially from the retracted to the extended position relative to the inner cylinder.

Patent Cooperation Treaty, international publication no. WO 90/00073 dated 11 Jan., 1990, discloses a single-use injection needle, in particular for dental applications. The syringe comprises a handle including a piston and a support part for a sleeve having an interlocking structure through which the piston extends. The syringe also comprises a syringe body having a tubular end with an inter-locking structure cooperating with that of the sleeve of the handle. The shape is adapted to interlock with the sleeve, and a protecting shell having a locking section capable of covering the tubular end and the sleeve so that they are locked in their interlocking position. The protective shell is adapted for sliding along the syringe body between two extreme positions, i.e. a forward position where it totally covers the injection needle and a pulled-back position where it frees it and covers the interlocked tubular end and sleeve.

SUMMARY OF THE INVENTION

The invention is directed to a dental syringe for use with a carpule comprising: (a) a hollow barrel; (b) a handle and plunger adapted to reciprocate within the barrel, the end of the plunger removed from the handle being adapted to releasably engage with a first end of a carpule; (c) a carpule receiving cavity at one end of the barrel in alignment with the plunger; and (d) engagement means at the end of the barrel opposite the handle and plunger for releasably engaging a second end of a carpule.

In the dental syringe as described, a coil spring may fit between the barrel and a portion of the plunger. The plunger may movably extend through a cap which holds the spring within the barrel.

The invention is also directed to a dental syringe and carpule combination comprising: (a) a hollow barrel; (b) a handle and plunger adapted to reciprocate within the barrel, the end of the plunger removed from the handle being adapted to releasably engage with a first end of a piston; (c) a carpule receiving cavity at one end of the barrel in alignment with the plunger; (d) head engagement means at the end of the barrel opposite the handle and plunger for releasably engaging a second end of a carpule; (e) a hollow carpule containing liquid having at a first interior end a piston which is adapted to releasably engage with the plunger, and at a second interior end thereof a head which is adapted to releasably engage with the head engagement means, and means on the head for enabling a double pointed dental needle to be releasably affixed to the end of the head; (f) a double pointed needle, one end of the needle penetrating into the interior of the carpule and the other end extending from the end of the head, whereby when the pigton is moved by the plunger in the direction of the head and needle, liquid from the carpule is pumped through the needle, and when the plunger and piston reach the end of the second end of the oarpule, the piston engages the head so that when the plunger and piston are moved in the direction away from the head and needle, the head and needle are withdrawn into the interior of the carpule.

An end of the piston proximate the plunger can be adapted with means for releasably engaging the plunger. The double pointed needle can be releasably secured to the head at the second end of the carpule by threads, and the piston can engage the head by rotating the handle, plunger and piston. The double pointed needle can have a needle hub at the mid-section thereof, the needle hub being adapted to releasably engage with the needle end of the head.

The head can have at one end thereof threads which releasably engage with the needle hub, and at the opposite end thereof threads which releasably engage with the end of the piston opposite the plunger engaging end. The head can have threads which are adapted to releasably engage with the end of the barrel removed from the plunger and handle.

The plunger can have formed in one end thereof releasable means which are adapted to engage the corresponding releasable means in the piston, and the piston can have formed at the end of the piston opposite the plunger releasable engagement means which enable the piston to releasably engage the head, and move the piston, head, needle hub and needle rearwardly within the interior of the carpule by rotating the plunger and handle clockwise or counterclockwise to disengage the head, needle hub and needle from the end of the barrel.

The carpule can have positioned in one interior end thereof, a piston and seal combination, and in the opposite end thereof, a head and seal means. The dental syringe as described can include an adapter which releasably engages with the carpule, the barrel and the head.

The invention is also directed to an anaesthetic carpule for use with a dental syringe, comprising: (a) a hollow cylindrical ampule casing; (b) a piston enclosed in the interior of one end of the ampule casing, the piston means having at each end thereof respective releasable engagement means; and (c) a head at the interior end of the ampule casing opposite the piston, the head having a needle engaging means protruding from the end thereof, in the direction opposite to the piston, the head being adapted to engage with the needle end of the barrel of a dental syringe and the head being adapted to be releasably engaged by the engagement means of the piston when the piston is moved against the head.

In the carpule as described, one of the releasable engagement means on the piston can be adapted to be engaged with a plunger of a dental syringe. The piston engagement means, the head engagement means and the needle engagement means can be threads which are adapted to engage corresponding thread adjoining components.

The Carpule can include a needle which has a needle hub which has a female thread on the interior thereof, adapted to engage with a male thread on the head, said head also having a male thread on the exterior thereof, the thread being adapted to engage with a female thread formed on the interior of a dental syringe barrel. The needle and needle hub can be enclosed in a protective cover.

BRIEF DESCRIPTION OF THE DRAWINGS

In drawings which illustrate specific embodiments of the invention, but which should not be construed as restricting the spirit or scope of the invention in any way:

FIG. 6 illustrates an enlarged frontal partial section view of the plunger engaged with the piston, which is engaged with the head and the needle hub.

FIG. 7 illustrates an enlarged frontal partial section view of the plunger, piston, head, and needle hub assembly partially withdrawn into the interior of the carpule.

FIG. 8 illustrates an enlarged exploded frontal section view of the plunger, piston, head, and needle hub components of the modified dental syringe.

FIG. 9 illustrates an enlarged exploded frontal section view of an alternative embodiment of modified dental syringe with modified seals.

FIG. 11 illustrates an enlarged frontal partial section view of an alternative embodiment of the modified dental syringe, wherein the carpule is front loaded into the dental syringe.

FIG. 12 illustrates an enlarged frontal partial section view of the alternative embodiment of the modified front-loaded dental syringe, the plunger being engaged with the piston and the cover 14 being removed from the needle.

FIG. 13 illustrates an enlarged frontal partial section view of the alternative embodiment of the modified front-loaded dental syringe, wherein the plunger and piston have engaged the head and partially withdrawn the needle into the interior of the carpule.

FIGS. 14a to 14j illustrate ten sequential schematic front views of the modified dental syringe.

FIG. 14a illustrates the carpule being loaded into the dental syringe.

FIG. 14b illustrates the carpule being rotated one half turn counterclockwise to engage the threaded end of the carpule with the threaded end of the syringe.

FIG. 14c illustrates the needle, hub and cover being engaged with the threaded end of the syringe by a counterclockwise rotation of the cover.

FIG. 14d illustrates the stem being engaged in the piston of the carpule by a clockwise rotation of the handle.

FIG. 14e illustrates the cover being removed by unscrewing the cover from the needle.

FIG. 14f illustrates the anaesthetic in the carpule being aspirated and injected by depressing the handle and plunger.

FIG. 14g illustrates the piston being engaged in the needle and head assembly by turning the handle clockwise.

FIG. 14h illustrates the needle and head assembly being withdrawn into the interior of the carpule by withdrawing the handle.

FIG. 14i illustrates the handle and plunger being unscrewed from the piston in the carpule by a counterclockwise rotation of the handle.

FIG. 14j illustrates the carpule being removed from the dental syringe with the needle being contained in the carpule.

DETAILED DESCRIPTION OF SPECIFIC EMBODIMENTS OF THE INVENTION

Figures 1, 2, 3:
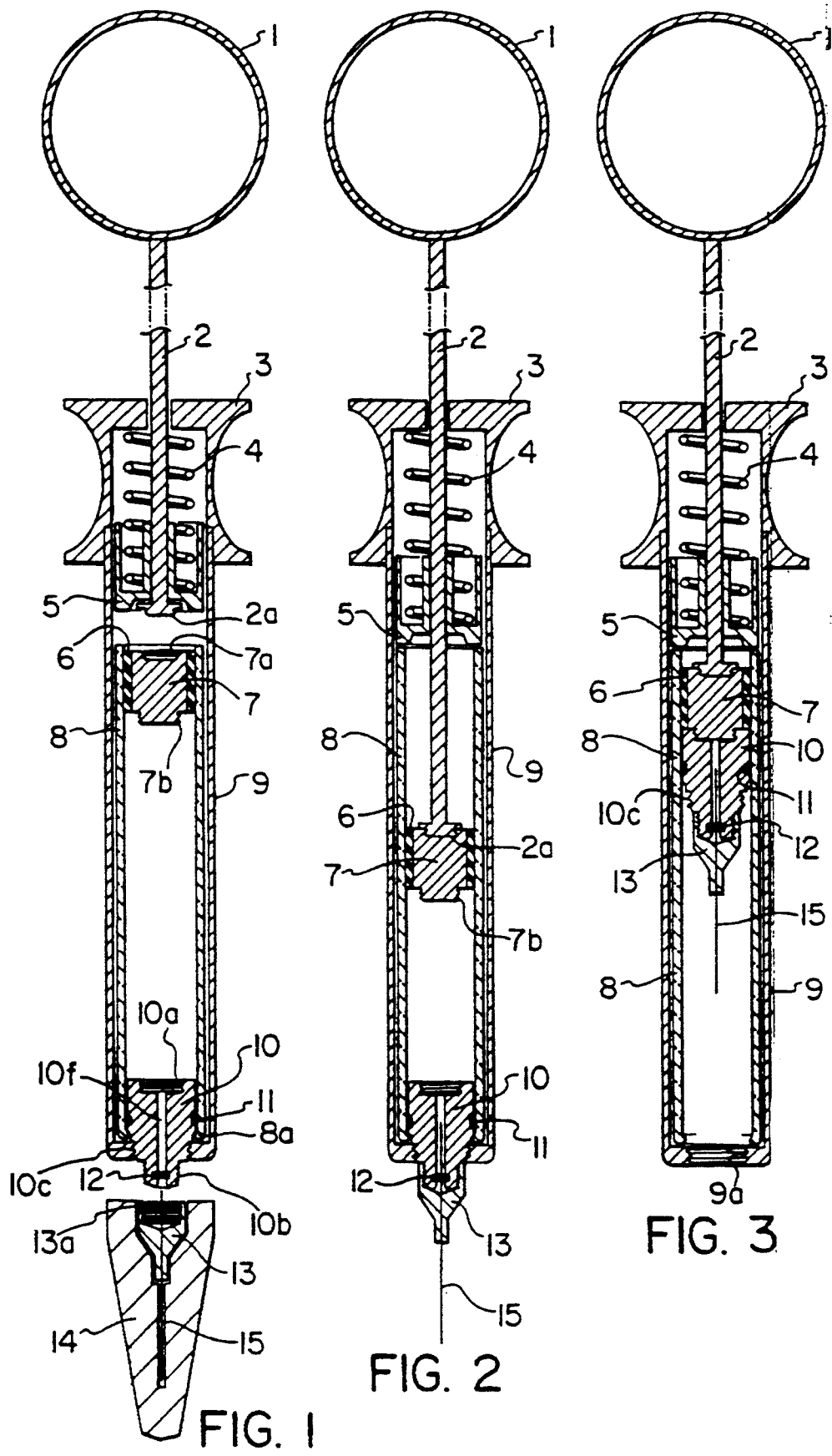
FIG. 1 illustrates a frontal partial section view of the modified dental syringe with a carpule loaded into the syringe.
FIG. 2 illustrates a frontal partial section view of the modified dental syringe with a plunger pushing the piston in the interior of the carpule.
FIG. 3 illustrates a frontal partial section view of the piston having engaged the head and needle hub and withdrawn the needle into the interior of the carpule.
Figure 4:
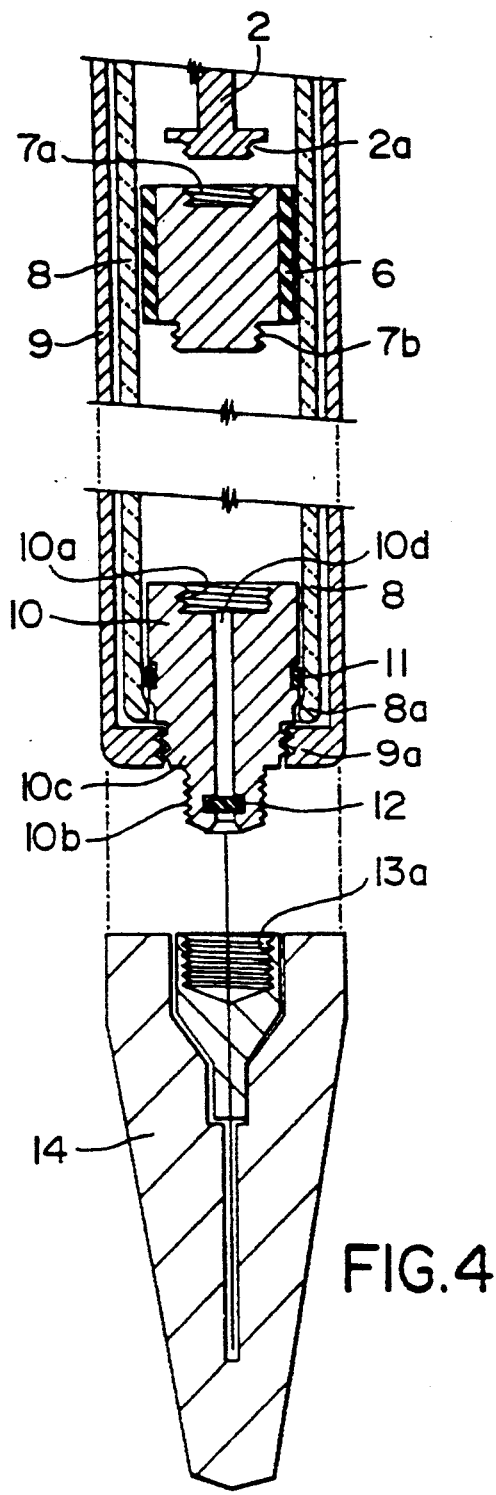
FIG. 4 illustrates an enlarged frontal partial section view of the plunger, piston, head and needle hub assembly.
Figure 5:
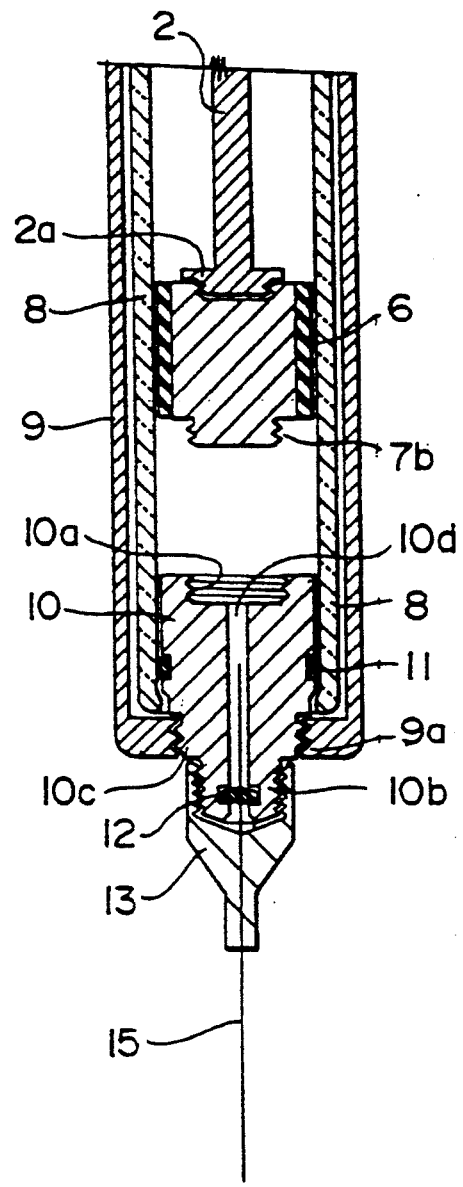
FIG. 5 illustrates an enlarged frontal partial section view of the needle hub engaged with the head tip and the plunger engaged with the piston.

Referring to FIG. 1, which illustrates a frontal partial section view of the modified dental syringe and carpule assembly, the dental syringe is comprised of a handle 1 with a plunger 2, the plunger 2 sliding reciprocally through the interior of a finger grip 3. A coil spring 4 is positioned in an interior cavity of the grip 3. The spring 4 is held in place by a cap 5, which has a lip at the upper edge (not shown) which holds the cap 5 in place. The end of the plunger 2, opposite the handle, has a male thread in the end thereof. The barrel 9 is connected to the grip 3 by threads (not shown). The barrel 9 is hollow and is adapted to hold therein a carpule assembly. The carpule assembly is constructed of a hollow glass ampule 8, and a piston 7 therein which has around the circumference thereof a piston seal 6. The piston 7 and seal 6 fit within one end of the interior of the hollow cylindrical glass ampule 8. The piston 7 has formed therein at the end proximate to the male thread 2a (or plug) of the plunger 2 a female piston thread 7a (or a plug receiving cavity). At the opposite end of the piston 7, there is formed a male thread 7b.

Positioned in the interior of the ampule 8 at the end opposite the piston 7 is a hollow head 10 which has at one end proximate to the piston 7 a female thread 10a, which is adapted to mate with male thread 7b of piston 7. The head 10 has at the opposite end thereof a male thread 10b. A canal 10f is formed through the centre of the head 10. A ring head seal 11 surrounds the head 10 and seals the head 10 with the interior of the glass ampule 8. A membrane 12 seals the internal canal 10f which is formed in the interior of the head 10. The head 10 has around the mid-section thereof a male thread 10c which is adapted to mate with a corresponding female thread 9a formed in the end of the barrel 9. The carpule assembly is supplied as a unit.

A needle hub 13, which has a needle 15 penetrating therethrough, and a cover 14, which protects one end of the needle 15, are assembled together and supplied as a unit. The needle hub 13 has formed in one end thereof a female thread 13a, which is adapted to engage releasably with male thread 10b of head 10.

Referring to FIG. 2, which illustrates a frontal partial section view of the modified dental syringe assembly, the plunger 2, and the male thread or plug 2a, at the end thereof, has been engaged with female thread or cavity 7a of the piston 7. The piston 7 has been pushed by the plunger 2 partway down the interior of the ampule 8. This action forces liquid (anaesthetic) in the interior of the ampule 8, out through the needle 15.

FIG. 3 illustrates a frontal partial section view of the position of the modified dental syringe after the male thread 7b of the piston 7 has been engaged by a rotating turn with the female thread 10a of the head 10, after the male thread 10c has been disengaged by corresponding rotating turn from female thread 9a at the end of the barrel 9.

FIGS. 4, 5, 6 and 7 illustrate enlarged frontal partial section views of the modified dental syringe during various stages of operation. The carpule assembly consists of a glass ampule 8 at one end of which is located the piston assembly 7 and at the opposite end the head assembly 10. Liquid to be injected is contained between the piston 7 and the head 10. The carpule is loaded in the conventional manner by pulling back on the handle 1 which pulls out the plunger 2 and the cap 5 assembly allowing sliding of the carpule assembly into the barrel 9.

As the carpule is placed in the barrel 9, it is rotated 178 turn counterclockwise so as to lock its head thread 10c in the barrel thread 9a. The needle assembly consisting of the needle hub 13 and its cover 14 is then placed on the end of the syringe and screwed in a clockwise motion onto the protruding male part of the head thread 10b. This screwing motion attaches the needle hub 13 to the head 10 of the carpule and tightens the carpule by tightening its male head thread 10c into the female barrel thread 9a. The needle head cover 14 is removed and disposed of. The plunger 2 is then lowered onto the carpule's piston 7 and the tip of the plunger 2a is screwed into the short piston female thread 7a of piston 7 with a clockwise motion. The dental syringe is now ready for aspirating and injecting of the anaesthetic.

As the injection is given, piston 7 is pushed down the ampule 8 until it reaches the head 10. At this point, the handle 1 is turned clockwise and the piston male thread 7b screws into the female head thread 10a. As the handle 1 is turned, the male thread 7b bottoms out in female thread 10a. The male head thread 10c then proceeds to unscrew from the female barrel thread 9a. A single assembly consisting of the piston 7, the head 10, and the needle hub 13 is now attached to the plunger 2.

At this point, the handle 1 is withdrawn and the piston 7, head 10 and needle hub 13 assembly is pulled up the ampule 8. As the end of travel is reached, the plunger thread 2a hits the cap 5. The handle 1 is then unscrewed counterclockwise releasing the plunger thread 2a from the female piston thread 7a and the rest of the head 10, needle 15 assembly which is now inside the ampule 8. The handle 1 is pulled back against spring 4 and the ampule 8 with the needle assembly inside falls out or can be removed and disposed of.

FIG. 8 illustrates an enlarged exploded frontal section view of a slightly modified version of the plunger, piston, head, and needle hub components of the modified dental syringe. As seen in FIG. 8, two O-ring seals 6a and 6b encircle the piston 7, rather than the tubular piston seal 6 illustrated in the previous drawings. The head 10 has an O-ring seal 11 around it. Membrane 12 seals the canal 10f. Otherwise, the construction of this version of the modified dental syringe is substantially the same as previously discussed and illustrated.

FIG. 9 illustrates an enlarged exploded frontal section view of an embodiment of modified dental syringe with modified seals. In the embodiment illustrated in FIG. 9, the membrane 12 is located at the top of the canal 10f in the head 10, rather than at the bottom as indicated in FIG. 8. In certain situations, it may be preferred to have the needle 15 penetrate most of the length of the canal 10f, before puncturing the membrane 12.

Figure 10:
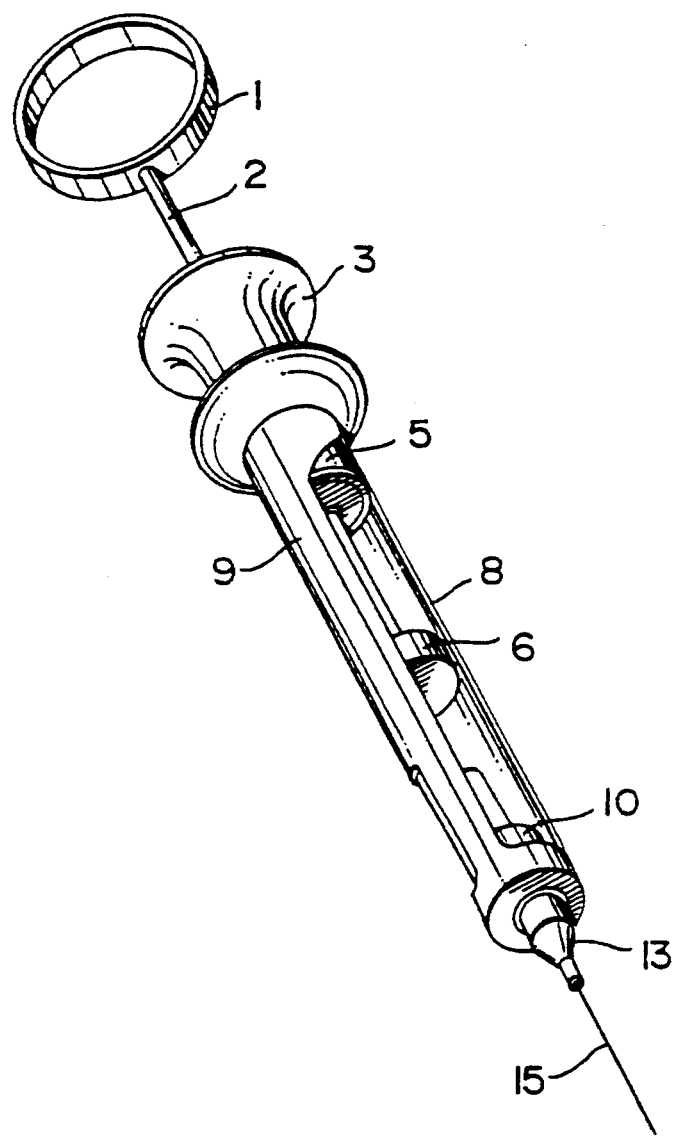
FIG. 10 illustrates an isometric perspective view of the modified dental syringe, without the carpule.

FIG. 10 illustrates an isometric view of the modified dental syringe, without the carpule. The handle 1, plunger 2, finger grip 3, and cap 5 are readily visible. The piston seal 6 rides within the interior of the barrel 9. The top end of the head 10 is also visible. The needle hub 13 and needle 15 are attached to the end of the barrel 9.

FIGS. 11, 12 and 13 illustrate enlarged frontal partial section views in successive stages of operation an alternative front-loading embodiment of the modified dental syringe. In this version, the carpule is front-loaded into the dental syringe. FIG. 12 illustrates the plunger being engaged with the piston 7 and the cover 14 being removed from the needle 15. FIG. 13 illustrates the plunger 2 and piston 7 engaged with the head 10 and the needle 15 partially withdrawn into the interior of the carpule 8.

For the front end carpule loading system illustrated in FIGS. 11, 12 and 13, an adapter 16 is secured by a lip 16c to the end of the carpule 8. Adapter 16 has on the exterior circumference thereof male threads 16a which engage with female threads 9a of the barrel 9. The adapter 16 has on the interior thereof female threads 16b which mate with male threads 10c of head 10. In the embodiment illustrated in FIGS. 11, 12 and 13, the needle hub 13 is shaped slightly differently from the needle hub 13 illustrated in the previous embodiment illustrated in FIGS. 1 through 9 inclusive. However, the male hub 13 could have the same shape if required. Similarly, head 10 has a slightly altered shape from that shown in the previous embodiments. Again, however, the function of the head 10 and the three sets of threads formed therein, 10a, 10c and 10d, are basically the same. The main difference between the embodiment illustrated in FIGS. 11, 12 and 13 is the presence of adapter 16, which permits the ampule 8 to be loaded in the front end of the barrel 9.

OPERATION

FIGS. 14a to 14j illustrate ten sequential schematic front views of the modified dental syringe. FIG. 14a illustrates the carpule being loaded into the dental syringe. FIG. 14b illustrates the carpule being rotated one half turn counterclockwise to engage the threaded end of the carpule with the threaded end of the syringe. FIG. 14c illustrates the needle, hub and cover being engaged with the threaded end of the syringe by a counterclockwise rotation of the cover, FIG. 14d illustrates the stem being engaged in the piston of the carpule by a clockwise rotation of the handle. FIG. 14e illustrates the cover being removed by unscrewing the cover from the needle. FIG. 14f illustrates the anaesthetic in the carpule being aspirated and injected by depressing the handle and plunger. FIG. 14g illustrates the piston being engaged in the needle and head assembly by turning the handle clockwise. FIG. 14h illustrates the needle and head assembly being withdrawn into the interior of the carpule by withdrawing the handle. FIG. 14i illustrates the handle and plunger being unscrewed from the piston in the carpule by a counterclockwise rotation of the handle. FIG. 14j illustrates the carpule being removed from the dental syringe with the needle being contained in the carpule.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A dental syringe and carpule combination comprising:
   (a) a hollow elongated barrel having a first end and a second end;
   (b) a handle, spring and piston plunger combination, said plunger having a first end and a second end, the first end being adjacent the handle, said plunger reciprocating within the barrel, the handle slidably extending through the first end of the barrel, the second end of the plunger removed from the handle releasably engaging with a first end of a piston in the carpule;
   (c) a carpule receiving cavity in the barrel proximate to the second end of the barrel in alignment with the plunger;
   (d) threaded carpule head engagement means at the second end of the barrel opposite the handle and plunger for releasably engaging corresponding threads on a second end of a carpule;
   (e) a hollow liquid containing carpule having a piston end proximate to the second end of the plunger and a head end proximate to the second end of the barrel, the carpule having in a first interior end thereof a slidable piston which at a first end releasably engages with the second end of the plunger, and at a second opposite end releasably engages with the head end of the carpule, the head end of the carpule having threads for releasably engaging with the carpule head engagement means of the barrel, and threads on the carpule head for enabling a correspondingly threaded hub of a double pointed dental needle to be releasably affixed to an exterior end of the head;
   (f) a double pointed hollow needle and hub threadedly engaged with the threads on the head of the carpule, one end of the needle penetrating into the interior of the carpule and the other end extending from the end of the carpule head and the second end of the barrel, whereby when the piston is engaged and moved by the plunger in the direction of the carpule head and needle, liquid in the carpule is pumped through the hollow of the needle, and when the plunger and piston reach the end of the second head end of the carpule, the second end of the piston engages the carpule head so that when the handle, plunger and piston are rotated, the head and needle are threadedly disengaged from the second end of the barrel and when the handle, plunger and piston are moved in a direction away from the second end of the barrel, the carpule head and needle are withdrawn into the interior of the carpule.

2. A dental syringe according to claim 1 wherein the second end of the plunger proximate the piston has threads thereon which releasably engage with corresponding mating threads in the first end of the piston for releasably engaging the plunger with the piston.

3. A dental syringe according to claim 2 wherein the double pointed needle is releasably secured to the head at the second end of the carpule by left hand threads, and the piston has at the second end proximate the carpule head, right hand threads which engage corresponding mating threads of the carpule head by rotating the handle, plunger and piston in a right handed manner.

4. A dental syringe according to claim 3 wherein the double pointed needle has a needle hub at the mid-section thereof, the needle hub having threads for releasably engaging with corresponding mating threads on a needle end of the carpule head.

5. A dental syringe according to claim 4 wherein the carpule head has at an exterior end thereof male threads which releasably engage with mating female threads of the needle hub, and the carpule head at an opposite interior end thereof has female threads which releasably engage with mating male threads at the second end of the piston opposite the first plunger engaging end.

6. The dental syringe according to claim 5 wherein the carpule head has on the exterior end thereof male threads which releasably engage with mating female threads in the second end of the barrel removed from the plunger and handle.

7. A dental syringe according to claim 6 wherein the plunger has formed in the second end thereof male thread means which releasably engage with mating corresponding female threads in the first end of the piston, and the piston has formed at the second end opposite the plunger male threads which enable the piston to releasably engage mating female threads in an interior end of the carpule head, and move and retract the piston, head, needle, hub and needle into the interior of the carpule by rotating the plunger and handle clockwise or counterclockwise to disengage the head, needle hub and needle from the female threads in the end of the second end of the barrel.

8. A dental syringe according to claim 7 wherein the carpule has positioned in one interior end thereof, a piston and seal combination, and in the opposite end thereof, a head and seal means.

9. A dental syringe according to claim 1 including an adapter which releasably engages with the carpule, the barrel and the head.

10. An anaesthetic carpule for use with a dental syringe comprising:
    (a) a hollow cylindrical carpule casing having a first end and a second end;
    (b) a piston enclosed in the interior of the first end of the carpule casing, the piston having a first end thereof first releasable engagement means and at a second end thereof second releasable engagement means; and
    (c) a head having a first interior end and a second exterior end at the second end of the carpule casing opposite the piston, the head having a threaded needle engaging means protruding from the second end thereof, in a direction opposite to the piston, the head having on an exterior thereof second threads which releasably engage with mating threads of a needle end of a barrel of a dental syringe, and the head releasably engaging with the second engagement means of the second end of the piston when the piston is moved against the first interior end of the head.

11. A carpule according to claim 10 wherein the releasable engagement means on the first end of the piston are threads which releasably engage with corresponding threads on a plunger of a dental syringe.

12. A carpule according to claim 11 wherein the first releasable engagement means at the first end of the piston, and the second releasable engagement means at the second end of the piston are threads.

13. A carpule according to claim 12 including a hollow needle which has thereon a needle hub which has a female thread on the interior thereof, the female thread of the hub releasably engaging with a first male thread protrusion of the second exterior end of the head, said head also having a second male thread on the exterior thereof, the second thread releasably engaging with a female thread formed on an interior of an open end of a dental syringe barrel opposite a handle and plunger of the barrel.

14. A carpule according to claim 13 wherein the needle and needle hub are enclosed in a protective cover.

15. A carpule according to claim 13 wherein the first thread needle engagement means and the second exterior threads on the head are opposite to the threads of the releasable engagement means at the first end of the piston and the releasable engagement means at the second end of the piston.

16. A carpule according to claim 15 wherein the releasable engagement means of the first end of the piston is a right hand female thread, the releasable engagement means of the second end of the piston is a right hand male thread, the releasable engagement means of an interior end of the head is a right hand female thread, and the second thread on the exterior of the head is a left hand male thread.

* * * * *